United States Patent
Rezaei

(10) Patent No.: US 11,596,667 B2
(45) Date of Patent: Mar. 7, 2023

(54) METHOD FOR TREATING OR PREVENTING IDIOPATHIC POLYPOIDAL CHOROIDAL VASCULOPATHY (IPCV)

(71) Applicant: IVERIC bio, Inc., Parisppany, NJ (US)

(72) Inventor: Kourous Rezaei, Chicago, IL (US)

(73) Assignee: IVERIC bio, Inc., Parsippany, NJ (US)

( * ) Notice: Subject to any disclaimer, the term of this patent is extended or adjusted under 35 U.S.C. 154(b) by 0 days.

(21) Appl. No.: 16/764,718

(22) PCT Filed: Nov. 16, 2018

(86) PCT No.: PCT/US2018/061459
§ 371 (c)(1),
(2) Date: May 15, 2020

(87) PCT Pub. No.: WO2019/099786
PCT Pub. Date: May 23, 2019

(65) Prior Publication Data
US 2021/0169975 A1      Jun. 10, 2021

Related U.S. Application Data

(60) Provisional application No. 62/587,126, filed on Nov. 16, 2017.

(51) Int. Cl.
| | |
|---|---|
| *A61K 38/17* | (2006.01) |
| *A61K 31/4709* | (2006.01) |
| *A61K 31/7105* | (2006.01) |
| *A61K 45/06* | (2006.01) |
| *C07K 16/18* | (2006.01) |
| *A61P 27/02* | (2006.01) |
| *A61P 27/06* | (2006.01) |

(52) U.S. Cl.
CPC ........ *A61K 38/179* (2013.01); *A61K 31/4709* (2013.01); *A61K 31/7105* (2013.01); *A61K 45/06* (2013.01); *A61P 27/02* (2018.01); *A61P 27/06* (2018.01); *C07K 16/18* (2013.01)

(58) Field of Classification Search
None
See application file for complete search history.

(56) References Cited

U.S. PATENT DOCUMENTS

| | | | |
|---|---|---|---|
| 2015/0017163 A1* | 1/2015 | Patel | A61P 35/00 424/134.1 |
| 2016/0038589 A1 | 2/2016 | Patel | |
| 2016/0296550 A1* | 10/2016 | Patel | A61K 31/7088 |
| 2017/0015740 A1 | 1/2017 | Rother et al. | |

OTHER PUBLICATIONS

Risitano and Marotta, Am J Hematol. 2018; 93: 564-5 (Year: 2018).*
Hussain and Ciulla, Expert Opinion on Emerging Drugs, 2017 vol. 22, No. 3, 235-246; https://doi.org/10.1080/14728214.2017. 1362390 (Year: 2017).*
The website downloaded on Oct. 22, 2021: https://www.asrs.org/patients/retinal-diseases/30/polypoidal-choroidal-vasculopathy; 5 pages total (Year: 2021).*
The website downloaded on Oct. 22, 2021: https://eyewiki.aao.org/Polypoidal_Choroidal_Vasculopathy; 11 pages total (Year: 2021).*
Piche-Nicholas et al., MAbs. 2018; 10: 81-94. doi: 10.1080/19420862. 2017.1389355 (Year: 2018).*
Kleinman et al., Complement Activation and Inhibition in Retinal Diseases. Dev Ophthalmol. 2016, vol. 55, pp. 46-56 (Author manuscript pp. 1-14). p. 6, para 2.
International Search Report and Written Opinion dated Feb. 27, 2019 in corresponding PCT International Application No. PCT/US2018/061459.

* cited by examiner

*Primary Examiner* — Christina M Borgeest
(74) *Attorney, Agent, or Firm* — Jon E. Gordon; Haug Partners LLP

(57) ABSTRACT

A method for treating or preventing idiopathic polypoidal choroidal vasculopathy is provided comprising intravitreal injections of Zimura™ (or another anti-C5 agent) and Eylea® (or another VEGF antagonist).

18 Claims, No Drawings
Specification includes a Sequence Listing.

SEQUENCE LISTING

```
<160> NUMBER OF SEQ ID NOS: 1

<210> SEQ ID NO 1
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-fluoro nucleotide
<220> FEATURE:
<221> NAME/KEY: modified_base
<222> LOCATION: (2)..(2)
<223> OTHER INFORMATION: 2'-OMe nucleotide
<220> FEATURE:
<221> NAME/KEY: modified_base
<222> LOCATION: (3)..(4)
<223> OTHER INFORMATION: 2'-fluoro nucleotide
<220> FEATURE:
<221> NAME/KEY: modified_base
<222> LOCATION: (6)..(6)
<223> OTHER INFORMATION: 2'-fluoro nucleotide
<220> FEATURE:
<221> NAME/KEY: modified_base
<222> LOCATION: (7)..(8)
<223> OTHER INFORMATION: 2'-OMe nucleotide
<220> FEATURE:
<221> NAME/KEY: modified_base
<222> LOCATION: (9)..(12)
<223> OTHER INFORMATION: 2'-fluoro nucleotide
<220> FEATURE:
<221> NAME/KEY: modified_base
<222> LOCATION: (13)..(15)
<223> OTHER INFORMATION: 2'-OMe nucleotide
<220> FEATURE:
<221> NAME/KEY: modified_base
```

```
<222> LOCATION: (16)..(16)
<223> OTHER INFORMATION: 2'-fluoro nucleotide
<220> FEATURE:
<221> NAME/KEY: modified_base
<222> LOCATION: (18)..(19)
<223> OTHER INFORMATION: 2'-fluoro nucleotide
<220> FEATURE:
<221> NAME/KEY: modified_base
<222> LOCATION: (20)..(22)
<223> OTHER INFORMATION: 2'-OMe nucleotide
<220> FEATURE:
<221> NAME/KEY: modified_base
<222> LOCATION: (23)..(25)
<223> OTHER INFORMATION: 2'-fluoro nucleotide
<220> FEATURE:
<221> NAME/KEY: modified_base
<222> LOCATION: (26)..(28)
<223> OTHER INFORMATION: 2'-OMe nucleotide
<220> FEATURE:
<221> NAME/KEY: modified_base
<222> LOCATION: (29)..(31)
<223> OTHER INFORMATION: 2'-fluoro nucleotide
<220> FEATURE:
<221> NAME/KEY: modified_base
<222> LOCATION: (33)..(35)
<223> OTHER INFORMATION: 2'-fluoro nucleotide
<220> FEATURE:
<221> NAME/KEY: modified_base
<222> LOCATION: (36)..(36)
<223> OTHER INFORMATION: 2'-OMe nucleotide
<220> FEATURE:
<221> NAME/KEY: modified_base
<222> LOCATION: (37)..(37)
<223> OTHER INFORMATION: 2'-fluoro nucleotide
<220> FEATURE:
<221> NAME/KEY: modified_base
<222> LOCATION: (38)..(38)
<223> OTHER INFORMATION: 2'-OMe nucleotide
<220> FEATURE:
<221> NAME/KEY: modified_base
<222> LOCATION: (39)..(39)
<223> OTHER INFORMATION: Inverted deoxy thymidine

<400> SEQUENCE: 1
cgccgcgguc ucaggcgcug agucugaguu uaccugcgt                    39
```

METHOD FOR TREATING OR PREVENTING IDIOPATHIC POLYPOIDAL CHOROIDAL VASCULOPATHY (IPCV)

CROSS-REFERENCE TO RELATED APPLICATIONS

This application is the National Stage entry under 35 U.S.C. § 371 of International Application No. PCT/US2018/061459 filed on Nov. 16, 2018, published on May 23, 2019 under Publication No. WO 2019/099786 A1, which claims the benefit of U.S. Provisional Application No. 62/587,126 filed on Nov. 16, 2017, the entireties of which are herein incorporated by reference.

SEQUENCE LISTING

The instant application contains a Sequence Listing which has been submitted electronically in ASCII format and is hereby incorporated by reference in its entirety. Said ASCII copy, created on Nov. 16, 2017, is named A112 37 SL.txt and is 1,951 bytes in size.

FIELD OF THE INVENTION

This invention relates to methods and compositions useful for the treatment or prevention of an ophthalmological disease or disorder, namely idiopathic polypoidal choroidal vasculopathy (IPCV), comprising administration of an effective amount of Zimura™ (or another anti-C5 agent) in combination with a VEGF antagonist (such as Avastin®, Eylea®, or Lucentis®).

BACKGROUND OF THE INVENTION

Idiopathic polypoidal choroidal vasculopathy (IPCV) is a disease of the choroid that can cause severe loss of central vision. It is characterized by the presence of polypoidal vascular lesions with or without an associated vascular network (Yannuzzi, et al., 1990). Clinical features of IPCV include leakage under the retinal pigment epithelium (RPE) which causes a pigment epithelial detachment (PED), leakage into the subretinal space, recurrent subretinal hemorrhage and serous retinal detachment (Yannuzzi et al., 1990). When leakage or hemorrhage occurs in the macular region, central vision loss ensues.

The disease is typically diagnosed with indocyanine green angiography (ICGA), where the presence of vascular dilations is identified (Spaide et al., 1995). These may not be seen on fluorescein angiography (FA), which may reveal only leakage from ill-defined choroidal neovascularization (CNV). From an epidemiologic standpoint, IPCV is more prevalent in pigmented individuals, representing 23% of presumed neovascular age-related macular degeneration (NVAMD) in patients of Asian descent (Sho et al., 2003).

The fluorescein angiography (FA) findings in IPCV usually mimics ill-defined CNV in NVAMD, and consequently, visualization of the abnormal polypoidal lesions with ICGA is required to differentiate IPCV from CNV in NVAMD (Spaide et al., 1995).

IPCV will be defined by the presence of single or multiple focal areas of hyperfluorescence arising from the choroidal circulation within the first six minutes after injection of ICG, with or without an associated branching vascular network (Spaide et al., 1995). The presence of orange-red subretinal nodules with corresponding hyperfluorescence in ICGA is pathognomonic of IPCV and should be present. Spectral domain optical coherence tomography (SD-OCT) imaging may help visualizing the polypoidal lesions as dome-shaped anterior elevation of highly reflective RPE layers with regions of low to moderate reflectivity beneath the RPE line. SD-OCT may also help in the detection of subretinal fluid and PED that can reflect the activity of IPCV and will be useful in monitoring the response to treatment.

Currently, intravitreal administrations of anti-VEGF agents (Lucentis®, Avastin® or Eylea®) alone or in combination with photodynamic therapy (PDT) are the standard of care for IPCV. VEGF is the most potent inducer of permeability in biologic systems (50,000 times greater than Histamine) (Dvorak et al., 1995). The visual benefit from anti-VEGF administration results primarily from its effect on anti-permeability or leakage (Kang et al., 2014).

Unlike typical NVAMD eyes, where anti-VEGF monotherapy allows for potent anti-permeability effects, visual stabilization, and temporary neovascular quiescence in many cases, multiple studies demonstrate that anti-VEGF therapy may not be as effective in IPCV. While subretinal exudation may respond to anti-VEGF therapy with visual stabilization, the choroidal vascular changes on ICGA may persist despite VEGF inhibition (Gomi et al., 2008; Hikichi et al., 2013; Kokame et al., 2010; Lai et al., 2008; Marcus et al., 2013). Photodynamic therapy (PDT) in combination with anti-VEGF therapy has been shown to be effective in improving vision and inducing polyp regression, but the high recurrence rate and known complications of recurrent PDT administration render both PDT monotherapy and the combination of PDT with anti-VEGF agents unattractive. (Gomi et al., 2010; Lai et al., 2008; Ruamviboonsuk et al., 2010; Saito et al., 2013). This combination of stubborn vascular lesions with a potentially suboptimal treatment response leaves tremendous unmet need in IPCV.

The mechanism behind anti-VEGF resistance in eyes with IPCV remains unclear, but there is evolving literature that suggests genetic abnormalities in the complement system may be associated with the development of IPCV. A comprehensive meta-analysis found variants at ARMS2/HTRA1 (rs10490924, OR=2.27, p<0.00001; rs11200638, OR=2.72, p<0.00001), CFH (r51061170, OR=1.72, p<0.00001; rs800292, OR=2.10, p<0.00001) or the complement pathway (C2; rs547154, OR=0.56, p=0.01) were significantly associated with IPCV, with higher odds ratio observed at variants in ARMS2/HTRA1 (Chen et al., 2012). In addition, a recent meta-analysis of the association between I62V and IPCV and/or NVAMD was performed from eight studies involving 5,062 subjects. The I62V polymorphism showed a significant association with IPCV.

A meta-analysis of 13 published studies proposed that patients who are homozygous for complement factor H (CFH) polymorphism Y402H experience a reduced response to anti-VEGF treatment (Chen et al., 2015). A direct relationship between VEGF and CFH was recently demonstrated where VEGF upregulated CFH expression and VEGF inhibition lead to a decrease in CFH expression in RPE cells (Keir et al., 2017). Mice who received anti-mouse VEGF treatment, showed a significant decrease in VEGF and CFH. This led to a 200-fold increase in retinal C3 RNA and increased C5b-9 expression suggesting that VEGF inhibition may contribute to complement activation (Keir et al., 2017). Furthermore, aqueous humor samples collected 48 hours after intravitreal injection of bevacizumab demonstrated a decrease in VEGF levels but an increase in C3a, C4a, and C5a levels (Keir et al., 2017).

Taken together, these findings may potentially indicate that although VEGF inhibition has potent anti-permeability characteristics, it may also contribute to complement activation by reducing CFH expression and therefore limiting its full therapeutic potential in improvement of vision in IPCV patients. By inhibiting the complement system with Zimura™ (or another anti-C5 agent) in concert with anti-VEGF therapy, novel biomarkers of combination drug activity and superior functional outcomes may be achieved.

Zimura™, a PEGylated RNA aptamer, is an inhibitor of complement activation. It inhibits C5, a central component of the complement cascade, which plays multiple roles in innate immunity and inflammatory diseases. Inhibition of this key step in the complement cascade at the level of C5 prevents the formation of key terminal fragments (C5a and C5b-9) regardless of which pathway (alternate, classical or lectin) induced their generation. The C5a fragment is an important inflammatory activator inducing vascular permeability, recruitment and activation of phagocytes. C5b is involved in the formation of MAC: C5b-9, which initiates cell lysis. By inhibiting these C5-mediated inflammatory and MAC activities, therapeutic benefit may be achieved in IPCV.

In a phase 1 ascending dose and parallel group clinical trial the safety, tolerability, and pharmacokinetic profile of multiple intravitreal injections of Zimura™ in combination with Lucentis® 0.5 mg was evaluated in subjects with Neovascular AMD.

Zimura™ was well-tolerated and no particular safety concerns were identified. No significant evidence of intraocular inflammation, retinal vasculitis, or choroidal vasculopathy was evident. One patient was noted to develop a mild cataract, which was considered to be related to study drug by the investigator; despite this event, the visual acuity improved in this patient during the study.

Visual acuity (VA) assessments were primarily safety assessments to detect any decrease in vision associated with the intravitreal injections. There were no safety issues identified through measurement of VA. Assessment of VA was focused on the treatment-naïve (TN) patient subgroup of 43 patients who had received 6 injections at doses of 0.3 mg, 1 mg or 2 mg. There was a mean increase in VA (number of ETDRS letters) from Baseline at all time points for patients in the 0.3, 1 and 2 mg dose groups in the TN subgroup who received 6 injections. At Week 24, there was an improvement in mean VA from Baseline of 13.6 ETDRS letters for the 0.3 mg dose group, 11.7 ETDRS letters for the 1 mg dose group and 15.3 ETDRS letters for the 2 mg dose group.

Fifty-one percent (51%) of patients in the TN subgroup (n=43 patients) gained ≥15 ETDRS letters at Week 24. This included 6 patients (46%) in the 0.3 mg dose group, 7 patients (47%) in the 1 mg dose group, and 9 patients (60%) in the 2 mg dose group gaining ≥15 ETDRS letters of VA.

A separate phase 1 study was also performed in subjects diagnosed with geographic atrophy (GA). In this study, a total of 47 subjects were enrolled, in the 0.3 mg dose arm (n=24) and 1 mg dose arm (n=23). Subjects received treatment with 3 initial intravitreal injections of Zimura™ 0.3 mg/eye or 1 mg/eye, administered at Day 0, Week 4 and Week 8 with a follow up visit at Week 16. Subjects received 2 subsequent injections at Week 24 and Week 36 followed by a final follow up visit at Week 48. Standard safety assessments were performed for ophthalmic variables that included VA, TOP, ophthalmic examination, fundus autofluorescence (FAF), Fluorescein Angiography (FA), and optical coherence tomography (SD-OCT) together with adverse events (AEs), vital signs and laboratory variables.

Zimura™ was well tolerated and there were no AEs considered to be related to Zimura™. Fifteen subjects (32%) had AEs, predominantly Eye Disorder AEs in the study eye, assessed to be related to the injection procedure. The most frequently reported AEs were conjunctival hemorrhage (4 subjects, 9%), corneal edema (4 subjects, 9%), and dry eye (3 subjects, 6%). No other study eye AEs were reported by more than 2 subjects. The majority of AEs were mild or moderate in severity. There were 2 subjects with AEs of severe intensity: gastrointestinal inflammation and nasopharyngitis.

Vital signs and laboratory assessments did not show any particular clinically significant patterns or changes. Study eye ophthalmic examinations did not indicate any unexpected clinical findings. There were some transient findings post-injection (conjunctiva/sclera and cornea) that resolved prior to the next injection. Vitreous haze was also reported for a few subjects. Intraocular pressure (IOP) showed a small mean increase following injections but no indication of any cumulative increases.

VA assessments did not show any safety signals. There was suggestion of a drug exposure and dose related slowing of the rate of GA growth during the period of increased frequency of drug exposure (i.e. monthly dosing for 3 months) from Baseline to Week 24, as well as a suggestion of stabilized VA, including VA under low light conditions. The data supported further investigation of Zimura™ in larger clinical trials.

In another study, the safety and tolerability of Zimura™ intravitreal injection in combination with VEGF therapy was evaluated in subjects with idiopathic polypoidal choroidal vasculopathy (IPCV). Subjects included in the study were treatment experienced (prior treatment with anti-VEGF monotherapy of ≥8 injections in the previous 12 months) of either gender aged 50 years or above with diagnosis of IPCV. Subjects received 3 monthly intravitreal injections of Zimura™ (1 mg/eye) in combination with intravitreal injection of anti-VEGF agent (Avastin® 1.25 mg/eye or Lucentis® 0.5 mg/eye or Eylea® 2 mg/eye).

A total of 4 subjects were enrolled in this clinical trial and all the subjects completed the study. None of the subjects had a VA loss of more than 15 ETDRS letters at Month 3. There were no deaths during the study. There was one SAE of endophthalmitis reported in 1 subject. The SAE resolved and was assessed to be related to the injection procedure. None of the ocular AEs were assessed to be related to Zimura™ or anti-VEGF treatment. The intravitreal administration of Zimura™ in combination with an anti-VEGF agent (Avastin®, Eylea®, or Lucentis®) in patients with IPCV was generally well tolerated.

SUMMARY OF THE INVENTION

The present invention relates to methods useful for the treatment or prevention of an ophthalmological disease or disorder, particularly IPCV.

The present invention provides methods for treating or preventing IPCV, comprising administering to a subject in need thereof: (a) Zimura™ (or another anti-C5 agent) and (b) Eylea® (or another VEGF antagonist such as Avastin® or Lucentis®), wherein Zimura™ and Eylea® are administered in an amount that is effective for treating or preventing IPCV.

DETAILED DESCRIPTION OF THE INVENTION

Definitions

The term "VEGF" refers to a vascular endothelial growth factor that induces angiogenesis or an angiogenic process.

As used herein, the term "VEGF" includes the various subtypes of VEGF (also known as vascular permeability factor (VPF) and VEGF-A) (see FIGS. 2(A) and (B)) that arise by, e.g., alternative splicing of the VEGF-A/VPF gene including VEGF121, VEGF165 and VEGF189. Further, as used herein, the term "VEGF" includes VEGF-related angiogenic factors such as PlGF (placenta growth factor), VEGF-B, VEGF-C, VEGF-D and VEGF-E, which act through a cognate VEFG receptor (i.e., VEGFR) to induce angiogenesis or an angiogenic process. The term "VEGF" includes any member of the class of growth factors that binds to a VEGF receptor such as VEGFR-1 (Flt-1), VEGFR-2 (KDR/Flk-1), or VEGFR-3 (FLT-4). The term "VEGF" can be used to refer to a "VEGF" polypeptide or a "VEGF" encoding gene or nucleic acid.

The term "effective amount," when used in connection with an ophthalmological disease of IPCV, refers to an amount of the compositions of the invention comprising Zimura™ (or another anti-C5 agent) and Eylea® (or another VEGF antagonist) that is useful to treat or prevent IPCV. The "effective amount" can vary depending upon the mode of administration, specific locus of the ophthalmological disease, the age, body weight, and general health of the mammal.

Unless indicated otherwise, all percentages and ratios are calculated by weight based on the total weight of the composition.

Zimura™ is a PEGylated RNA aptamer consisting of a 13 kDa modified RNA aptamer that is conjugated at the 5' terminus to a ~43 kDa branched polyethylene glycol (PEG) moiety. The aptamer portion of Zimura™ is 39 nucleotides in length and modified with a primary amine at the 5' terminus to provide a reactive site for subsequent site specific conjugation ("PEGylation"). The nucleotide composition consists of 2' hydroxyl purines and modified 2' fluoro pyrimidines and 2' methoxy purines. The modified nucleotides minimize endonuclease digestion and contribute to activity. The 3' terminus is capped with an "inverted" 3'-3' phosphodiester linkage to a deoxythymidine nucleotide (idT) to minimize 3' exonuclease degradation. PEGylation is employed because it confers delayed clearance in vivo without diminishing affinity or activity. All concentrations and doses for Zimura™ (1 μM=13 μg/mL) are based on the mass of the aptamer, exclusive of the PEG mass.

Eylea® (aflibercept) is a recombinant fusion protein consisting of portions of human VEGF receptors 1 and 2 extracellular domains fused to the Fc portion of human IgG1 formulated as an iso-osmotic solution for intravitreal administration. Aflibercept is a dimeric glycoprotein with a protein molecular weight of 97 kilodaltons (kDa) and contains glycosylation, consisting of an additional 15% of the total molecular mass, resulting in a total molecular weight of 115 kDa. Aflibercept is produced in recombinant Chinese Hamster Ovary (CHO) cells.

VEGF Antagonists

In one embodiment, the VEGF antagonist is the antibody ranibizumab or a pharmaceutically acceptable salt thereof (see U.S. Pat. No. 7,060,269 (FIG. 1) for the heavy chain and light chain variable region sequences, which is hereby incorporated by reference in its entirety). Ranibizumab is commercially available under the trademark Lucentis.

In another embodiment, the VEGF antagonist is the antibody bevacizumab or a pharmaceutically acceptable salt thereof (see U.S. Pat. No. 6,054,29 for the heavy chain and light chain variable region sequences, which is hereby incorporated by reference in its entirety). Bevacizumab is commercially available under the trademark Avastin.

In another embodiment, the VEGF antagonist is aflibercept or a pharmaceutically acceptable salt thereof (Do et al. (2009) Br J Ophthalmol. 93:144-9, which is hereby incorporated by reference in its entirety). Aflibercept is commercially available under the trademark Eylea.

In one embodiment, the VEGF antagonist is tivozanib or a pharmaceutically acceptable salt thereof (U.S. Pat. No. 6,821,987, which is hereby incorporated by reference in its entirety).

In one embodiment, the VEGF antagonist is pegaptanib or a pharmaceutically acceptable salt thereof (U.S. Pat. No. 6,051,698 (FIG. 1), which is hereby incorporated by reference in its entirety). A composition comprising pegaptanib is commercially available under the trademark Macugen.

In another embodiment, the VEGF antagonist is sorafenib or a pharmaceutically acceptable salt thereof (Kernt et al. (2008) Acta Ophthalmol. 86:456-8, which is hereby incorporated by reference in its entirety). A composition comprising sorafenib is commercially available under the trademark Nexavar.

Anti-C5 Agent

In one embodiment, the anti-C5 agent is Zimura™ (avacincaptad pegol), also known as ARC1905. ARC1905 is a PEGylated RNA aptamer consisting of a 13 kDa modified RNA aptamer that is conjugated at the 5' terminus to a ~43 kDa branched polyethylene glycol (PEG) moiety. The aptamer portion of ARC1905 is 39 nucleotides in length and modified with a primary amine at the 5' terminus to provide a reactive site for subsequent site specific conjugation ("PEGylation"). The nucleotide composition consists of 2' hydroxyl purines and modified 2' fluoro pyrimidines and 2' methoxy purines. The modified nucleotides minimize endonuclease digestion and contribute to activity. The 3' terminus is capped with an "inverted" 3'-3' phosphodiester linkage to a deoxythymidine nucleotide (idT) to minimize 3' exonuclease degradation. PEGylation is employed because it confers delayed clearance in vivo without diminishing affinity or activity. All concentrations and doses for ARC1905 (1 μM=13 μg/mL) are based on the mass of the aptamer, exclusive of the PEG mass.

ARC1905 has the Structure Set Forth Below:

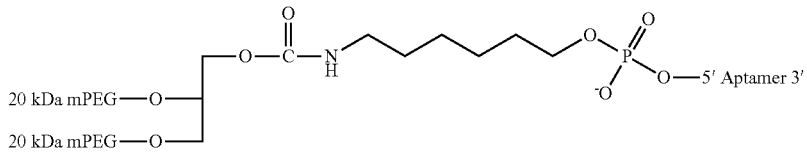

or a pharmaceutically acceptable salt thereof, where Aptamer fCmGfCfCGfCmGmGfUfCfUfC-mAmGmGfCGfCfUmGmAmGfUfCfUmGmAmGfUfU-fUAfCf CfUmGfCmG-3T (SEQ ID NO: 1) wherein fC and fU=2'-fluoro nucleotides, and mG and mA=2'-OMe nucleotides and all other nucleotides are 2'-OH and where 3T indicates and inverted deoxy thymidine. (U.S. Pat. No. 7,538,211 which is hereby incorporated by reference in its entirety). In some embodiments, each 20 kDa mPEG of the above structure has a molecular weight of about 20 kDa.

ARC1905 drug product is formulated at a concentration of 20 mg/mL (oligonucleotide mass) in phosphate buffered saline at pH 6.8-7.8 as a sterile aqueous solution. Sodium hydroxide or hydrochloric acid may be added for pH adjustment. ARC1905 drug product is presented in a USP Type I high recovery glass vial that contains a 0.5 mL v-shaped well sealed with fluorotec coated, halobutyl rubber stoppers and aluminum crimp seals. The product is supplied in single use vials and is preservative-free and intended for intravitreal injection only. The product should not be used if cloudy or if particles are present. Injection volume for each administration of ARC1905 is 0.1 mL (100 µL) providing a 2 mg/eye dose.

In other embodiments, the anti-C5 agent is Soliris® (eculizumab, U.S. Pat. No. 6,355,245 which is hereby incorporated by reference in its entirety) or LFG-316 (Novartis; US Patent Application No. 2010/0034809 which is hereby incorporated by reference in its entirety), or A217 (Quidel Corp., San Diego, Calif.).

Methods For Treating Or Preventing IPCV

The present invention provides new and improved methods and compositions for treating and preventing IPCV.

In one embodiment, Zimura™ (or another anti-C5 agent) is administered in combination with Eylea® (or another VEGF antagonist such as ranibizumab, bevacizumab, pegaptanib sodium, tivozanib, abicipar pegol or ESBA1008). The invention provides treatment regimens, including treatment and dosing regimens, related to the coadministration of Zimura™ (or another anti-C5 agent) and Eylea® (or another VEGF antagonist).

Zimura™ drug product is formulated at a concentration of 20 mg/mL (oligonucleotide mass) in phosphate buffered saline at pH 6.8-7.8 as a sterile aqueous solution. Sodium hydroxide or hydrochloric acid may have been added for pH adjustment. Zimura™ drug product is presented in a USP Type I high recovery glass vial that contains a 0.5 mL v-shaped well sealed with fluorotec coated, halobutyl rubber stoppers and red aluminum crimp seals. The product is preservative-free and intended for intravitreal injection only. The product should not be used if cloudy or if particles are present.

Zimura™ will be supplied in single use vials for intravitreal injection.

Injection volume for each administration of Zimura™ will be 0.1 mL (100 µL) providing a 2 mg/eye dose.

In some embodiments, Zimura™ (or another anti-CF agent) and Eylea® (or another VEGF antagonist) are administered within 24 hours of each other. In some embodiments, Zimura™ and Eylea® are administered on the same day. In some embodiments, Zimura™ and Eylea® are administered concurrently or sequentially. In some embodiments, Zimura™ is administered within about 1 min, about 2 min, about 5 min, about 10 min, about 15 min, about 20 min, about 25 min, about 30 min, about 40 min, about 50 min, about 60 min, about 90 min, about 2 hours, about 4 hours, about 6 hours, about 8 hours, about 12 hours, about 24 hours or about 48 hours of administration of Eylea®. In some embodiments, Eylea® is administered prior to administration of Zimura™. In other embodiments, Zimura™ is administered prior to administration of Eylea®. In some embodiments, Zimura™ is administered at least about 1 min, about 2 min, about 5 min, about 10 min, about 15 min, about 20 min, about 25 min, about 30 min, about 40 min, about 50 min, about 60 min, about 90 min, about 2 hours, about 4 hours, about 6 hours, about 8 hours, about 12 hours, about 24 hours or about 48 hours after administration of Eylea®. In some embodiments, Zimura™ and Eylea® are present in the same pharmaceutical composition and administered as a co-formulation.

In one aspect, a method for treating or preventing IPCV is provided, comprising administering to a subject in need thereof (a) a therapeutically effective amount of Zimura™, wherein Zimura™ is a pegylated or unpegylated aptamer and (b) Eylea®, wherein (a) and (b) are administered in an amount that is effective for treating or preventing IPCV, and wherein the administration comprises administering Eylea® followed by administration of about 2.0 mg of Zimura™ approximately 48 hours after administration of Eylea®.

In another aspect, a method for treating or preventing IPCV in treatment experienced subjects is provided. Treatment experienced is defined as 3 sequential Eylea® injections (or other antiVEGF agent) within the previous four (4) months with <1 line of visual improvement on the Snellen chart (not ETDRS chart) since the start of Eylea® treatment.

In another aspect of the invention, a method for treating or preventing IPCV is provided, comprising administering to a subject in need thereof (a) a therapeutically effective amount of Zimura™, wherein Zimura™ is a pegylated or unpegylated aptamer that binds to C5 complement and (b) Eylea®, wherein (a) and (b) are administered in an amount that is effective for treating or preventing IPCV, and wherein the administration comprises:

an induction phase administration period where Zimura™ and Eylea® are administered on Day 1, Month 1, and Month 2 in the following sequence, ±about seven days, wherein throughout said induction phase administration period a first dose of Eylea® is administered followed by an administration of Zimura™ on the same day and a second dose of Zimura™ is administered about 14 days later; and a maintenance phase administration period which occurs after the induction phase administration period wherein on Months 3, 5 and 7, Zimura™ is administered once monthly, and once every month on Months 4, 6, and 8, ±about seven days, wherein a single dose of Eylea® is administered followed by a single dose of Zimura™ on the same day. In another embodiment, an additional dose of Zimura™ is administered at months 4, 6, and 8 prior to the administration of Eylea and Zimura on the same day.

Example 1

Drug Supply
Zimura™
  Active Ingredient:
    Zimura™ is formulated as
    20 mg/mL solution for injection
  Excipients: Sodium Chloride, USP
    Sodium Phosphate Monobasic, Monohydrate, USP
    Sodium Phosphate Dibasic, Heptahydrate, USP
    Nitrogen, NF
    Sodium Hydroxide, NF (as needed)
    Hydrochloric acid, NF (as needed)
    Water for injection, USP
Dose and Administration
  Zimura™ is supplied in a single-use glass vial as noted above.
  Zimura™ and Eylea® will be injected without dilution.

Zimura™ is supplied in a single-use glass vial. To prepare for injection of Zimura™, use a 19 gauge filter needle (supplied) and a new 1-mL sterile syringe to withdraw about 0.2 mL of Zimura™ from the glass vial using aseptic technique. Remove the filter needle and replace it with the sterile 30-gauge injection needle (supplied). Expel any air bubbles and adjust the injection volume to 0.1 mL (100 μL).

Eylea® is a sterile, clear, and colorless pale yellow solution. Eylea® is supplied as a preservative-free, sterile, aqueous solution in a single-use, glass vial designed to deliver 0.05 mL (50 microliters) of Eylea® 2 mg (40 mg/mL in 10 mM sodium phosphate, 40 mM sodium chloride, 0.03% polysorbate 20, and 5% sucrose, pH 6.2). Eylea® will be administered in a total injection volume of 0.05 mL (50 μL). Intravitreal injections are administered according to the following regimens:

Induction Phase: Zimura™ and Eylea® are administered on Day 1, Month 1, and Month 2, 14 days apart:
Day 1: Eylea® 2 mg/eye followed by Zimura™ 2 mg/eye on the same day
Day 14: Zimura™ 2 mg/eye
Maintenance Phase:
Zimura™ 2 mg/eye is administered on Months 3, 5, and 7
Eylea® 2 mg/eye is administered followed by Zimura™ 2 mg/eye on the same day on Months 4, 6, and 8

Example 2

Zimura™ and Eylea® are supplied as noted in Example 1. They are administered according to the following regimen:

Induction Phase: Zimura™ and Eylea® are administered on Day 1, Month 1, and Month 2, 14 days apart:
Day 1: Eylea® 2 mg/eye followed by Zimura™ 2 mg/eye on the same day
Day 14: Zimura™ 2 mg/eye
Maintenance Phase:
Zimura™ 4 mg/eye (administered as two injections of Zimura™ 2 mg/eye) is administered on Months 3, 5, and 7
Zimura™ 2 mg/eye is administered, followed by, 2 days later, an administration of Eylea® 2 mg/eye followed by Zimura™ 2 mg/eye on the same day, on Months 4, 6, and 8.

Example 3

Visual acuity testing is performed at each visit using the procedure set forth in Example 2 of WO 2016/025313 (herein incorporated in its entirety by reference).

INCORPORATION BY REFERENCE

All publications and patent applications disclosed in this specification are herein incorporated by reference to the same extent as if each individual publication or patent application was specifically and individually indicated to be incorporated by reference.

What is claimed is:

1. A method for treating idiopathic polypoidal choroidal vasculopathy (IPCV), comprising administering to a subject in need thereof:
   (a) an anti-C5 agent and (b) a VEGF antagonist,
   wherein (a) and (b) are administered in an amount that is effective for treating IPCV,
   wherein the administering occurs for a first administration period induction phase followed by a second administration period maintenance phase wherein only the anti-C5 agent is administered monthly throughout the maintenance phase, and
   wherein the anti-C5 agent is a pegylated aptamer (avacincaptad pegol) with the following nucleotide sequence: fCmGfCfCGfCmGmGfUfCfUfCmAmGmGfCGfCf-UmGmAmGfUfCfUmG mAmGfUfUfUAfCf CfU-mGfCmG-3T (SEQ ID NO: 1), or a pharmaceutically acceptable salt thereof,
   wherein fC and fU=2'-fluoro nucleotides, and mG and mA=2'-OMe nucleotides and all other nucleotides are 2'-OH, and where 3T indicates an inverted deoxythymidine.

2. The method of claim 1 wherein the administering occurs once every month, ± about seven days, for a first administration period of at least three consecutive months, said first administration period comprises administration of (a) and (b) on the same day followed by administration of a subsequent dose of (a) after about 14 days.

3. The method of claim 2 wherein (a) and (b) are administered for a second administration period after completion of said first administration period, wherein (a) is administered at least once every month during said second administration period and (b) is administered once every other month together with administration of (a) during said second administration period.

4. The method of claim 3 wherein an additional dose of (a) is administered during said second administration period during months when (a) and (b) are both administered.

5. The method of claim 4 wherein said additional dose of (a) is administered about 48 hours before administering (a) and (b) on the same day.

6. The method of claim 3 wherein (a) and (b) are administered on the same day during the second administration period.

7. The method of claim 3 wherein avacincaptad pegol is administered intravitreally in an amount of 4.0 mg/eye once every month when (b) is not administered.

8. The method of claim 3 wherein the avacincaptad pegol or pharmaceutically acceptable salt thereof is administered intravitreally and in an amount of about 2.0 mg/eye.

9. The method of claim 8 wherein the VEGF antagonist is ranibizumab, bevacizumab, pegaptanib sodium, tivozanib, ESBA1008 or aflibercept.

10. The method of claim 9 wherein the VEGF antagonist is administered intravitreally.

11. The method of claim 10 wherein the VEGF antagonist is aflibercept and is administered in an amount of about 2 mg/eye, bevacizumab and is administered in an amount of about 1.25 mg/eye, or ranibizumab and is administered in an amount of about 0.5 mg/eye.

12. The method of claim 11 wherein the VEGF antagonist is aflibercept and is administered in an amount of about 2 mg/eye.

13. The method of claim 12 wherein avacincaptad pegol is administered intravitreally in an amount of 4.0 mg/eye once every month when (b) is not administered.

14. The method of claim 12 wherein avacincaptad pegol is administered after aflibercept during said first administration period.

15. The method of claim 14 wherein an additional dose of avacincaptad pegol is administered during said second administration period on months when avacincaptad pegol and aflibercept are both administered.

16. The method of claim 1 wherein (a) is administered after (b) during said first administration period.

17. The method of claim 1 wherein the avacincaptad pegol or pharmaceutically acceptable salt thereof is administered intravitreally and in an amount of about 2.0 mg/eye.

18. A method for treating idiopathic polypoidal choroidal vasculopathy (IPCV), comprising administering to a subject in need thereof: (a) an anti-C5 agent and (b) a VEGF antagonist, wherein (a) and (b) are administered in an amount that is effective for treating IPCV, and wherein the administering occurs for a first administration period induction phase followed by a second administration period maintenance phase wherein only the anti-C5 agent is administered monthly throughout the maintenance phase, wherein the anti-C5 agent is selected from the group consisting of eculizumab, LFG-316, and A217.

* * * * *